(12) United States Patent
Hampsch

(10) Patent No.: US 6,871,660 B2
(45) Date of Patent: Mar. 29, 2005

(54) PINCH VALVE AND METHOD OF OPERATING SAME

(75) Inventor: James Hampsch, Lafayette, IN (US)

(73) Assignee: Bioanalytical Systems, Inc., West Lafayette, IN (US)

( * ) Notice: Subject to any disclaimer, the term of this patent is extended or adjusted under 35 U.S.C. 154(b) by 157 days.

(21) Appl. No.: 10/175,580

(22) Filed: Jun. 19, 2002

(65) Prior Publication Data

US 2003/0234053 A1 Dec. 25, 2003

(51) Int. Cl.[7] .............................. F16K 7/06; F16K 11/16
(52) U.S. Cl. ............................. 137/1; 137/595; 251/7; 251/294
(58) Field of Search ..................... 137/1, 595, 625; 251/4, 7, 294

(56) References Cited

U.S. PATENT DOCUMENTS

| | | | |
|---|---|---|---|
| 2,339,036 A | * | 1/1944 | Tea ............................. 239/415 |
| 3,537,679 A | * | 11/1970 | Bulnes et al. ................ 251/144 |
| 3,882,899 A | | 5/1975 | Ginsberg et al. |
| 3,924,700 A | | 12/1975 | Lindsey et al. |
| 4,092,000 A | * | 5/1978 | Offutt, III .................... 239/532 |
| 4,172,580 A | | 10/1979 | Raftis et al. |
| 4,259,985 A | | 4/1981 | Bergmann |
| 4,524,802 A | * | 6/1985 | Lawrence et al. ........... 137/595 |
| 4,653,719 A | | 3/1987 | Cabrera et al. |
| 4,682,628 A | * | 7/1987 | Hill ........................ 137/624.11 |
| 4,694,861 A | | 9/1987 | Goodale et al. |
| 4,798,336 A | * | 1/1989 | Ilott ............................ 239/337 |
| 4,895,431 A | | 1/1990 | Tsujiuchi et al. |
| 4,978,101 A | * | 12/1990 | Nakaya et al. ......... 251/129.15 |
| 4,993,456 A | | 2/1991 | Sule |
| 5,048,556 A | | 9/1991 | Grumelot et al. |
| 5,098,060 A | | 3/1992 | Mogler et al. |
| 5,114,580 A | | 5/1992 | Ahmad et al. |
| 5,117,870 A | | 6/1992 | Goodale et al. |
| 5,265,840 A | | 11/1993 | Gillespie et al. |
| 5,343,884 A | | 9/1994 | Henderson et al. |
| 5,383,839 A | | 1/1995 | Bohls |
| 5,395,352 A | | 3/1995 | Penny |
| 5,464,388 A | | 11/1995 | Merte et al. |
| 5,499,657 A | | 3/1996 | Schmitt |
| 5,584,320 A | | 12/1996 | Skinkle et al. |
| 5,626,209 A | | 5/1997 | Viola |
| 5,640,988 A | | 6/1997 | Brereton |
| 5,657,960 A | | 8/1997 | Taylor |
| 5,704,584 A | | 1/1998 | Winterer et al. |
| 5,746,251 A | | 5/1998 | Bullard |

* cited by examiner

Primary Examiner—Stephen M. Hepperle
(74) Attorney, Agent, or Firm—Michael A. Swift; Doreen Gridley; Ice Miller

(57) ABSTRACT

A valve comprising valve members which are biased toward a closed or open position is provided with a flexible cable which is used to reposition the valve members by moving the cable so as to overcome the force generated by the biasing means. The cable may be moved by an appropriate actuator, such as a motor. When desired, the cable is moved to its original position allowing the biasing means to return the valve members to their original position. In one embodiment, the cable is slidably constrained within a flexible, non-compressible sleeve. The valve members according to one embodiment ensure complete closure of a resilient tube passing therethrough without the need to radially align the valve members.

18 Claims, 8 Drawing Sheets

PINCH VALVE AND METHOD OF OPERATING SAME

FIELD OF THE INVENTION

This invention relates to valves, and more particularly, to a pinch valve and a method of operating same.

BACKGROUND OF THE INVENTION

For many years, systems have been designed to carry fluids, both liquid and gas. In many of these systems, valves are critical considerations. They can be used to direct fluids to specific destinations, or to allow for isolation of components within a fluid carrying system for maintenance or replacement. In other systems, certain valves serve as safety features. In any system, from the most basic to the most intricate, the means for actuating the valve is a critical variable which must be appropriate to the specific application.

Several alternative means exist for effecting valve operations. One option is to manually manipulate the valve. For example, U.S. Pat. No. 5,265,840 discloses a manually operated pinch valve, where pressure is applied directly to a trigger, which is fixed to an actuator and pinching means, all of which are aligned in a substantially co-axial manner. Depressing the trigger therefore causes the actuator to operate against the force of a spring, thereby moving a dome block (pinching means) away from a resilient tube, allowing the tube to open. This type of application is suited for applications where an individual is holding an instrument which contains pinch valves.

Certain applications make it infeasible or impractical to manipulate the valve by human force as described above. Independent and/or remote operation is desired in many applications where the valve acts as a safety related isolating or activating means. For example, a standard safety feature for a system carrying a hazardous or dangerous composition, is to provide an actuator which isolates a leak in the system either automatically upon detection of the leak or by remote, manual means. Another example of a system in which a remotely or automatically actuated valve which is desired is a sprinkler system used to combat fires. An example of this type of remotely operated valve is disclosed in U.S. Pat. No. 5,343,884. This patent discloses a self closing gate valve which uses a compressed spring acting against a valve actuating arm to force the valve shut. The spring is held in a compressed position by clips and a sleeve. The spring is released either when the clips melt, as caused by a fire, or by manually retracting the sleeve from a remote location by use of a cable. Thus, should a fire break out, either the clips will melt, thereby allowing the spring to operate against the actuating arm, or if an individual discovers the fire prior to the melting of the clips, the individual discovering the fire can manually manipulate the cable, thereby moving the sleeve holding the spring to achieve the same valve operation. The valve in this type of system is designed for only a single operation, i.e., sprinkling due to a single fire. After the single operation, the system must be reset and parts (clips) replaced. Thus, while effective for a particular use, this type of system has very limited use in other applications, and even may be undesirable for its intended use since it is conceivable that a fire could follow another before an individual has an opportunity to repair or replace the valve.

In other applications, remote operation is primarily a function of the desire to automate a process for practicality, expediency, or efficiency. This type of system may use a motor operating either a cam or a gear to directly force the stem of a valve to the desired position. These systems are particularly useful in cases where it is desired to re-position the valve more than once, or in a particular sequence. For example, U.S. Pat. No. 5,584,320 discloses a motor driven device for control of fluid flow through a plurality of tubes. In this device, a plunger is held against a tube by a spring to stop the flow of fluid through a tube. To open the tube, a motor shaft turns a roller cage which results in rollers being forced against the plunger, thereby forcing the plunger away from the tube and allowing fluid to flow through the tube. By providing a plurality of concentric rollers, a single tube can be opened or shut in a predetermined pattern. Locating the rollers coaxially allows a series of tubes to be controlled.

Alternatives to the motor and cam system are available in solenoid and piston operated valves. Solenoid operated valves replace the motor and cam with a coil, a metal core, and activating current. The metal core either operates against the stem of the valve, or is the stem of the valve. Typically, a spring holds the stem in a first position. The magnetic field, when activated, forces the stem into a second position. Depending on the particular application, the valve may be normally open or normally shut when it is de-energized. U.S. Pat. No. 4,259,985, for example, discloses the use of a solenoid to operate a three-way pinch valve. Three-way pinch valves are well suited as a zero dead volume switch valves, meaning that a sample may be withdrawn from one location and directed to a second location with minimal waste of fluid. Systems utilizing a piston rely on a fluid, either liquid or gas, operating against a piston to reposition the valve. A fluid system is disclosed in U.S. Pat. No. 3,882,899 in conjunction with a three-way pinch valve designed to shut the initially open tube before allowing the initially shut tube to open.

Of course, for any given application, more than one type of actuator may be appropriate, and the actual choice will be driven by other considerations such as, but not limited to, cost, dependability, and availability of power. While all of these are effective in a wide variety of applications, recent developments within the fields of medical and pharmaceutical research highlight the shortcomings of the above systems.

The fields of medical and pharmaceutical research are laboratory intensive endeavors necessitating significant repetition of and alteration to specific experiments. One example of this is pharmacokinetics research. In this type of testing, it is not unusual to inject predetermined amounts of chemicals into a test animal at periodic intervals. The animal's body fluids, such as blood or bile, can then be sampled for the drug and drug metabolites to calculate the tissue concentrations. In experiments of this nature, it is desired to place the valves which control the sampling process as close to the animal as possible in order to minimize the amount of fluid which must be extracted in collecting the proper sample. Additionally, the valve must be as unobtrusive as possible, so that the animal's activities are not unduly altered, since the physical activity may be a significant element of the test. Pinch valves are particularly useful in these applications. Pinch valves can control fluid flow through resilient tubes without the need for contacting the fluid being controlled. Thus, the valve can be reused without fear of cross-contamination. Further, there is no need for special coatings on the valve, such as anticoagulation coating when the fluid is blood. As in any application, expenses, failures, and maintenance efforts must be kept to a minimum. As is explained below, each of the valve systems outlined above, even those which incorporate pinch valves, have shortcomings if used for this type of research.

The device of U.S. Pat. No. 5,265,840 must be manually activated. Consequently, an individual must be in close proximity to the animal resulting in changes to the test animal's behavior. Alternatively, the valves could be located away from the animal, requiring an extreme amount of fluid to be withdrawn in order to collect a sample. Further, the need for a coaxial relationship between the trigger, actuator, and pinching means significantly limits the potential for using this device in testing situations. Finally, such manual actuation requires that the individual be able to recognize and react (activate the valve) to changes in animal behavior instantaneously in order to properly control the fluids in the system.

Motor operated valves such as that disclosed in U.S. Pat. No. 5,584,320, also suffer from several deficiencies. It is difficult to miniaturize a valve, motor and cam so that they can be located near the animal. Even if such miniaturization were accomplished, a power line to the motor would be required. Such a power line is cumbersome and consumes precious space near the valve. Additionally, the motor and cam can be noisy, thereby distracting the animal. Further, the added complexity of the motor and cam increases costs both for initial acquisition and also for maintenance.

Piston operated valves suffer from the additional problem of requiring a complex support system. While it is possible to use a pressurized gas tank with a reducer to provide the working fluid, a complex system is required to automate the operation of the reducer. Alternatively, a support system capable of producing pressurized fluid may be purchased and maintained at increased expense. Further, the piston chamber increases the bulk of the valve assembly. A system utilizing piston operated valves is limited further by its susceptibility to leaks. Fluid leaking about the piston decreases performance of the system. Additionally, in order to move with a live animal, the tubing carrying the working fluid would have to be flexible, further complicating the system and increasing the propensity for leaking. Of course, many animals commonly used in testing have a propensity for gnawing. Considering the fact that a tube's flexibility is normally achieved by utilizing a pliable material, the tube becomes very susceptible to damage from being gnawed upon by the animals. Consequently, use of this type of system may result in exorbitant maintenance costs.

Solenoid operated valves present shortcomings similar to those found with motorized valves. While power lines can be reasonably lightweight, the coil and plunger of the valve must be made of ferrous material, resulting in a heavy and bulky valve. Further, the complexity of the valves means that they are expensive to manufacture and maintain, and may be susceptible to breakdown. A final shortcoming relates to the unfortunate gnawing tendency which was discussed above. Since there may be electricity present in the power line at the time an animal is gnawing on the power line, the consequences of a test animal gnawing through the insulation to the conductor can be quite detrimental to the health of the animal thereby interfering with the collection of data in addition to the added maintenance costs.

Therefore, it is desired to provide a valve which:
is inexpensive to manufacture and maintain;
is lightweight;
can be remotely operated;
is extremely reliable;
contains low dead volume;
is easily adapted for use with many control systems;
is free to move with respect to its activating mechanism;
does not require precise alignment or keying in order to ensure correct operation;
can be easily miniaturized.

SUMMARY OF THE INVENTION

In accordance with the present invention, a flexible cable is provided for repositioning valve members from an original position to an alternate position. In one embodiment, the invention is a pinch valve used for controlling fluid flow through a resilient tube. The pinch valve is biased toward either an open or a closed original position by a biasing means. The flexible cable is then put under tension, thereby overcoming the force of the biasing means so as to reposition the pinch valve to its alternate position. When in the closed position, the valve members ensure complete closure of a resilient tube passing therethrough without the need to radially align the opposing valve members because closure is accomplished by a scissor like engagement of the valve members.

In one embodiment the invention is a three-way remotely operated pinch valve comprising a cylindrical housing with two passages therethrough for passage of resilient tubing into which fluid may be introduced. A movable pinch bar is used to alternately pinch shut one of the two resilient tubes between the pinch bar and the inner edge of the passages. A spring is used to bias the pinch bar within the housing so that one tube is initially open and the other tube is initially closed. A flexible cable is attached at one end to the pinch bar. In one embodiment, a flexible, non-compressible sleeve surrounds the cable and is maintained in a fixed relationship to the pinch bar. The other end of the cable is connected to a remote actuator such as a solenoid or a servo motor and the other end of the sleeve is maintained in a fixed relationship to the actuator. By repositioning the solenoid or servo motor, the cable slides within the sleeve and acts against the pinch bar, overcoming the force of the biasing means and opening the initially closed tube and closing the initially open tube. Releasing the cable allows the biasing means to move the pinch bar to its original position, thereby returning the tubes to their original condition.

This invention provides a valve which is inexpensive to manufacture and maintain. Further, the entire valve can be lightweight while being extremely reliable. As a result of using a flexible cable within a flexible, non-compressible sleeve, there is no need for alignment of the actuating mechanism with the valve. Furthermore, the valve need not be maintained in a fixed position relative the actuating mechanism. This capability, combined with the ability to remotely operate the valve, makes the invention particularly valuable in live animal research applications. Since the invention is easily miniaturized and does not depend on a rigid relationship between the actuator and the valve, it is uniquely valuable in live animal research applications. Additionally, use of a cable allows embodiments of the invention wherein there is no delay between movement of the actuating mechanism and repositioning of the valve from open to closed or from closed to open.

DETAILED DESCRIPTION OF THE INVENTION

Figure 1:
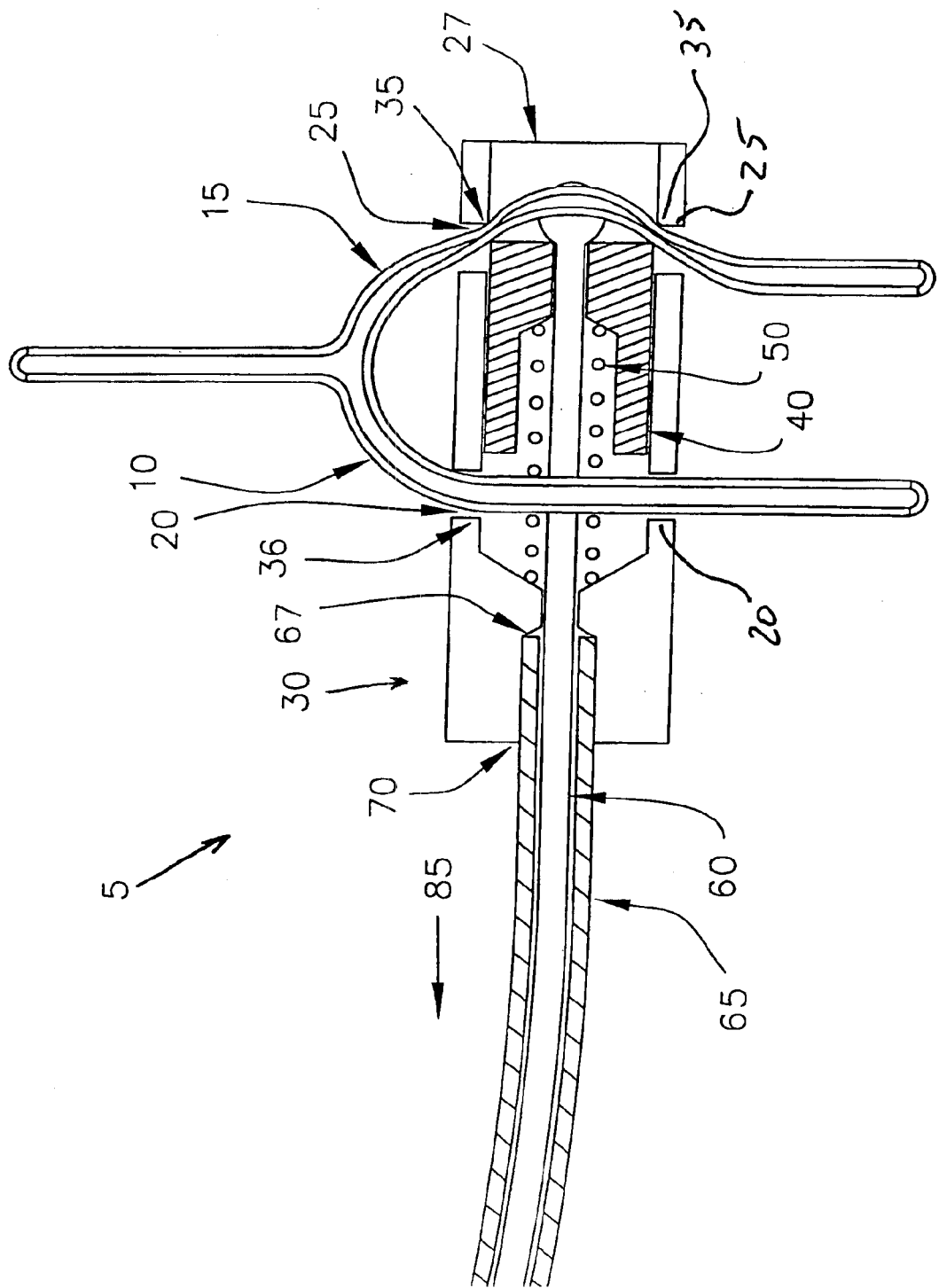
FIG. 1 is a sectional side view of one embodiment of a three-way pinch valve according to the present invention.
Figure 2:
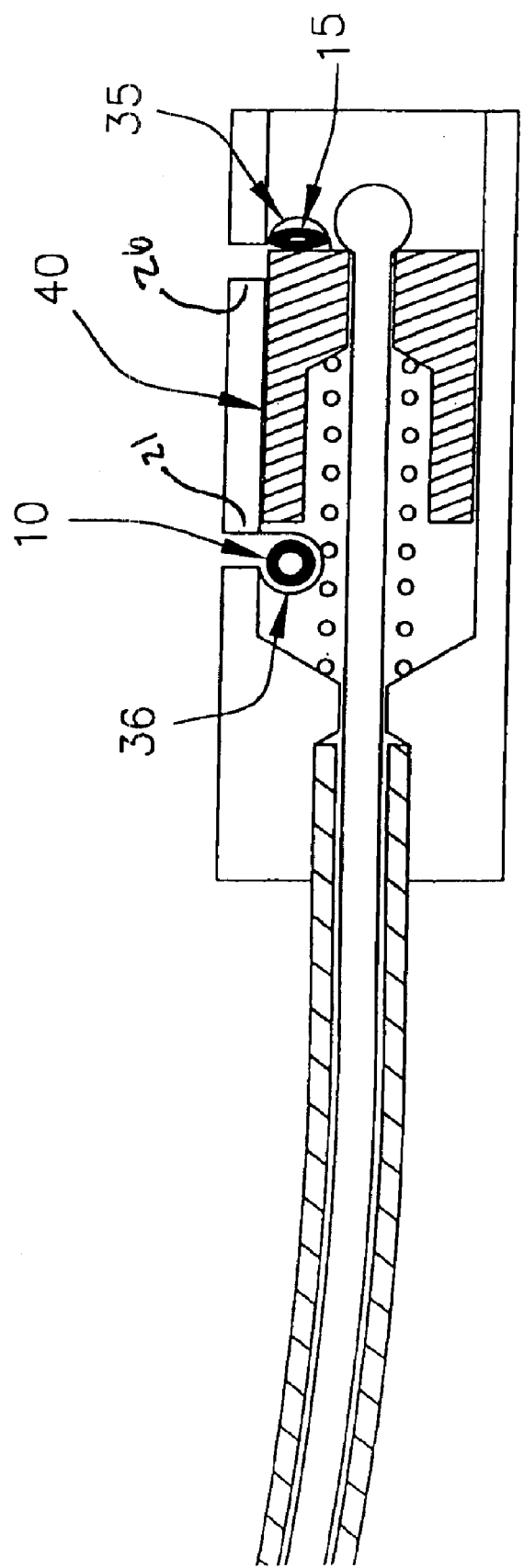
FIG. 2 is a sectional top view of the three-way pinch valve of FIG. 1.

Referring now to FIG. 1, a side sectional view of one embodiment of the invention as three way pinch valve 5 is shown. Housing 30 comprises first passageway 20 and second passageway 25. First and second resilient tubes 10 and 15, respectively pass through passageways 20 and 25 of housing 30. Tubes 10 and 15 are of the type to allow fluid(s) to pass therethrough and may comprise, for example, 0.025 inch outside diameter (OD) by 0.12 inch inside diameter (ID) polyurethane tubing manufactured by Braintree Scientific, Inc., of Braintree, Mass. In the embodiment of FIG. 1, passageways 20 and 25 are sized such that tubes 10 and 15 may be loaded from the side without threading the tubing through passageways 20 and 25. This is shown in FIG. 2, wherein passageways 20 and 25 comprise loading slots 21 and 26 respectively, loading slots 21 and 26 being sized such that resilient tubes 10 and 15 may be forced therethrough. While the embodiment of FIGS. 1 and 2 comprises loading slots 21 and 26, the scope of the present invention includes valves wherein the tubing must be threaded through a passageway.

Continuing with FIG. 1, housing 30 further comprises means for slidably accommodating 27 first valve member 40, which, in this embodiment, is shown in its first position. When first valve member 40 is in its first position, the first spaced opposing valve member pair comprising first valve member 40 and second valve member 35 of housing 30 is in its first or closed position. As seen in FIG. 1 and in FIG. 2, when the first spaced valve member pair comprising first valve member 40 and second valve member 35 is in the closed position, tube 15 is pinched shut such that fluid is not allowed to flow through tube 15.

Those of skill in the art will recognize that the embodiment of the invention shown in FIG. 1 provides a several significant improvements over other pinch valves. One such improvement, is that pinch valve 5 uses opposing valve members to create a scissor like action on tubes 10 and 15 to effect closing of tubes 10 and 15. Thus, primary valve member 40 is not required to be aligned so as to meet second valve member 35 in a flush relationship. Accordingly, there is no need to ensure radial alignment of valve member 40 to assure complete closure of a resilient tube. Moreover, in one embodiment, the scissoring effect is realized at two locations on a resilient tube as shown in FIG. 1, where valve member 40 is shown pinching tube shut against second valve member 35 at two locations.

Referring again to FIG. 1, the second spaced valve member pair comprising first valve member 40 and third valve member 36 is in its first or open position. As shown in FIG. 1 and FIG. 2, when the second spaced valve member pair comprising first valve member 40 and third valve member 36 is in the open position, tube 10 is not pinched shut such that fluid is allowed to flow through tube 10 when the second spaced valve pair is in its first position.

Continuing with FIG. 1, biasing means 50, which in this embodiment comprise a spring, is operably connected to housing 30 and first valve member 40 thereby forcing the first and second spaced valve member pairs comprising first valve member 40 and second valve member 35 and first valve member 40 and third valve member 36, respectively into their first positions. Those of skill in the art will appreciate that a number of structures will substitute as a means for biasing. By way of example, but not of limitation, it is possible to use cable 60 as the biasing means. The salient characteristic being the ability to ensure that the valve members are in a known position.

Returning to FIG. 1, cable 60, which may be of the type such as 0.024 inch OD, 7×7 construction stainless steel cable manufactured by SAVA Industries of Riverdale, N.J., passes through aperture 70 of housing 30 and is operably connected to first valve member 40. In this embodiment, cable 60 is slidably constrained by a means for constraining, namely sleeve 65 which is fixedly aligned with and passes through aperture 70 of housing 30.

Figure 3:
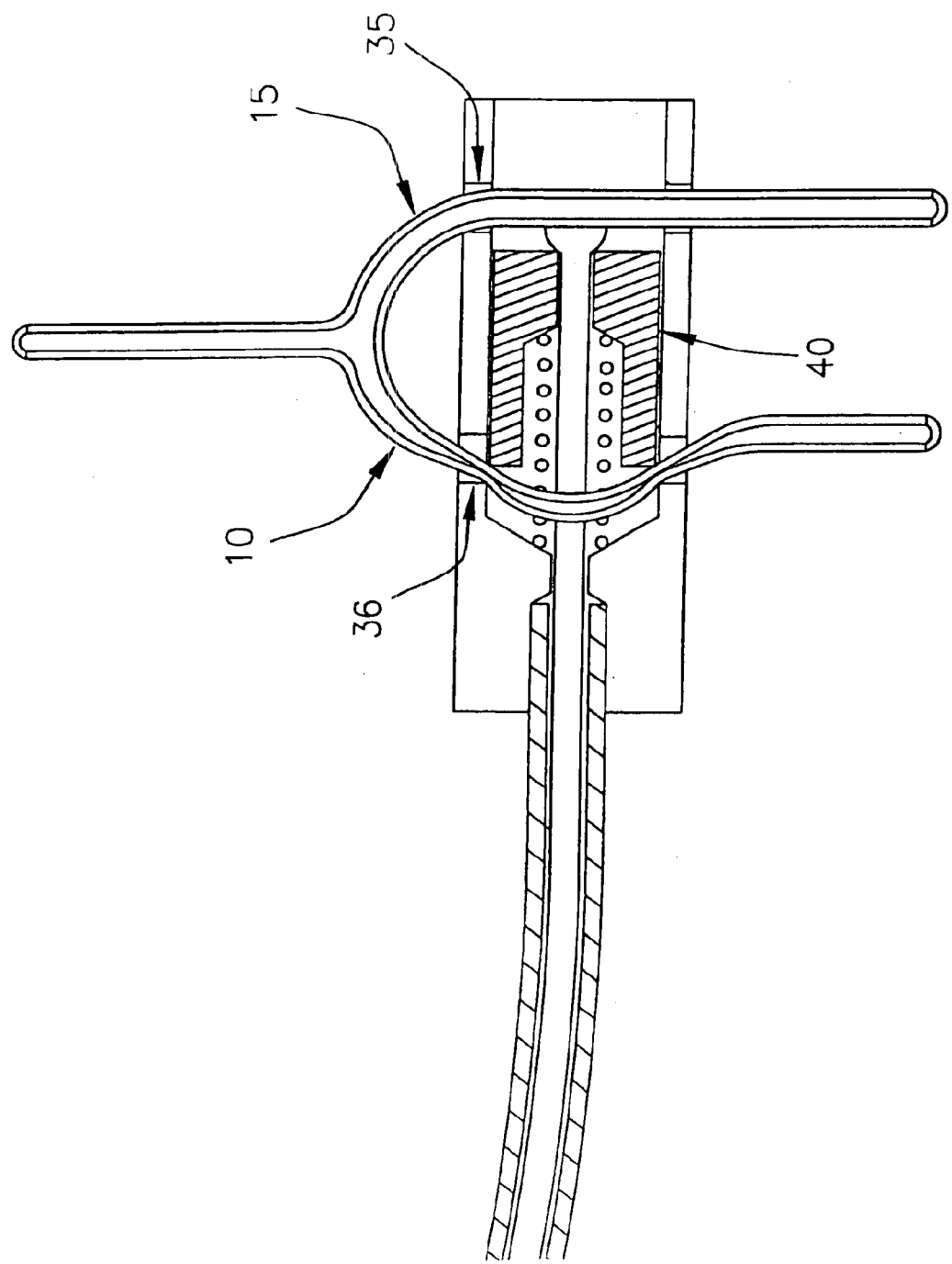
FIG. 3 is a sectional side view of the three-way pinch valve of FIG. 1 in an alternate position.
Figure 4:
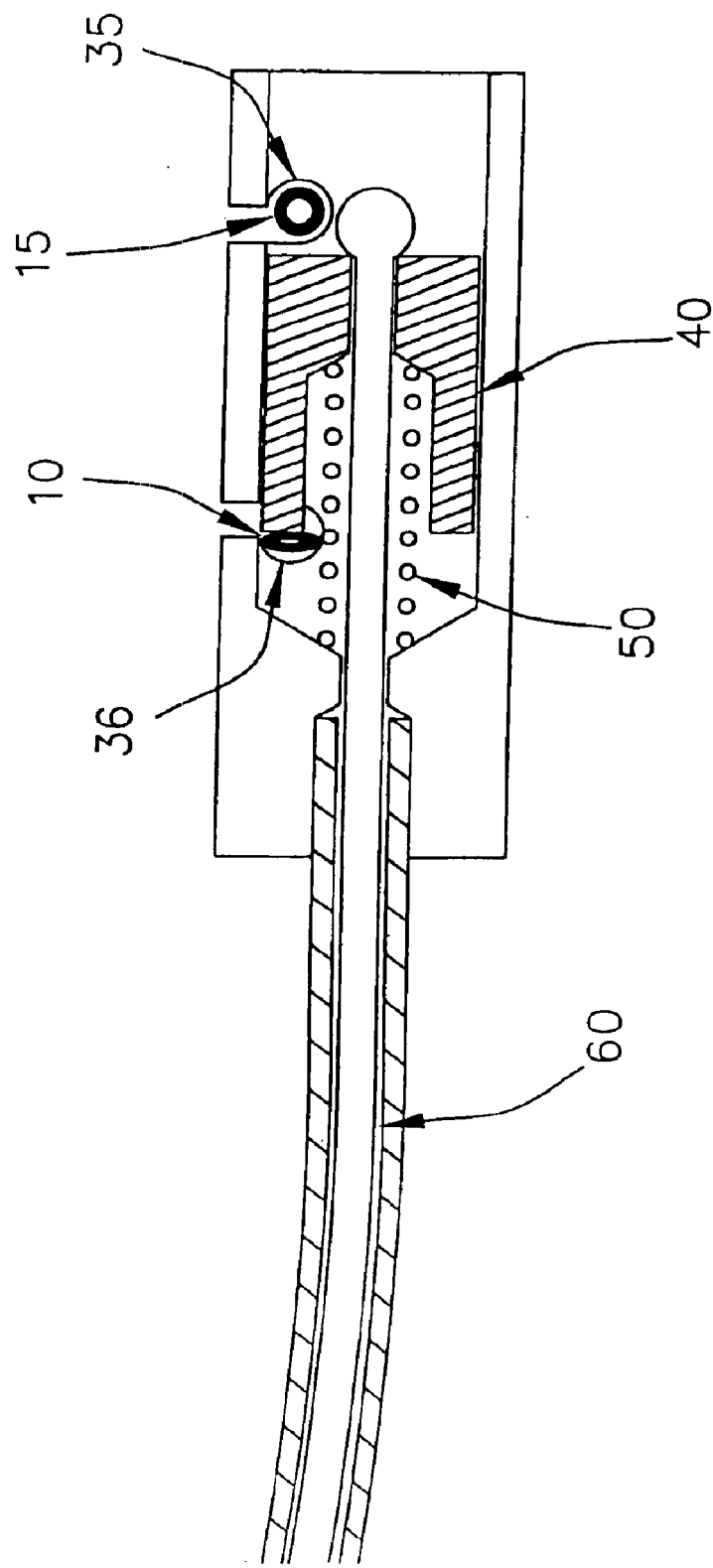
FIG. 4 is a sectional top view of the three-way pinch valve of FIG. 3.

FIG. 3 is a side sectional view of a three-way pinch valve with first valve member 40 in its second position, such that the first spaced valve member pair comprising first valve member 40 and second valve member 35 is in its second or open position. FIG. 4 shows that when the first spaced valve member pair comprising first valve member 40 and second valve member 35 is in the open position, tube 15 is not pinched shut such that fluid is allowed to flow through tube 15. Referring again to FIG. 3, the second spaced valve member pair comprising first valve member 40 and third valve member 36 is in its second or closed position. FIG. 4 shows that when the second spaced valve member pair comprising first valve member 40 and third valve member 36 is in the closed position, tube 10 is pinched shut such that fluid is not allowed to flow through tube 10.

First valve member 40 is placed in its second position by pulling cable 60 against first valve member 40 such that the force of biasing means 50 is overcome, and first valve member 40 moves from its first position to its second position.

According to one embodiment of the present invention, first valve member 40 may also be moved to positions intermediate its first position and its second position. When the first spaced valve member pair comprising first valve member 40 and second valve member 35 of housing 30 is in an intermediate position, tube 15 is pinched partially shut such that fluid flow through tube 15 is constrained, but fluid is allowed to flow through tube 15.

Although the embodiment of FIG. 4 shows biasing means 50 fixedly connected to first valve member 40 and cable 60 fixedly connected to first valve member 40, it will be appreciated by those of skill in the art that other structures such as, but not limited to, cable 60 fixedly attached to biasing means 50, may be used to practice the present invention, these embodiments being within the scope of the present invention. The salient characteristic being the ability to effect movement of first valve member 40 with respect to second and third valve members 35 and 36 respectively.

Those of skill in the art will further appreciate that the present invention may be practiced with a variety of pinch valve configurations. For example, the present invention may be practiced with a pinch valve wherein valve member 40 is sized such that when it is moved to a position intermediate its first position and its second position, tube 10 is not pinched and tube 15 is not pinched. This allows for both tubes to be open or either tube to shut. Additionally, pinch valve 5 may be modified such that at a position intermediate its first position and its second position, both tube 10 and tube 15 are pinched shut. This may be accomplished, by way of example but not of limitation, by the addition of springs and additional valve members to pinch valve 5 as is shown in FIG. 5.

Figure 5:
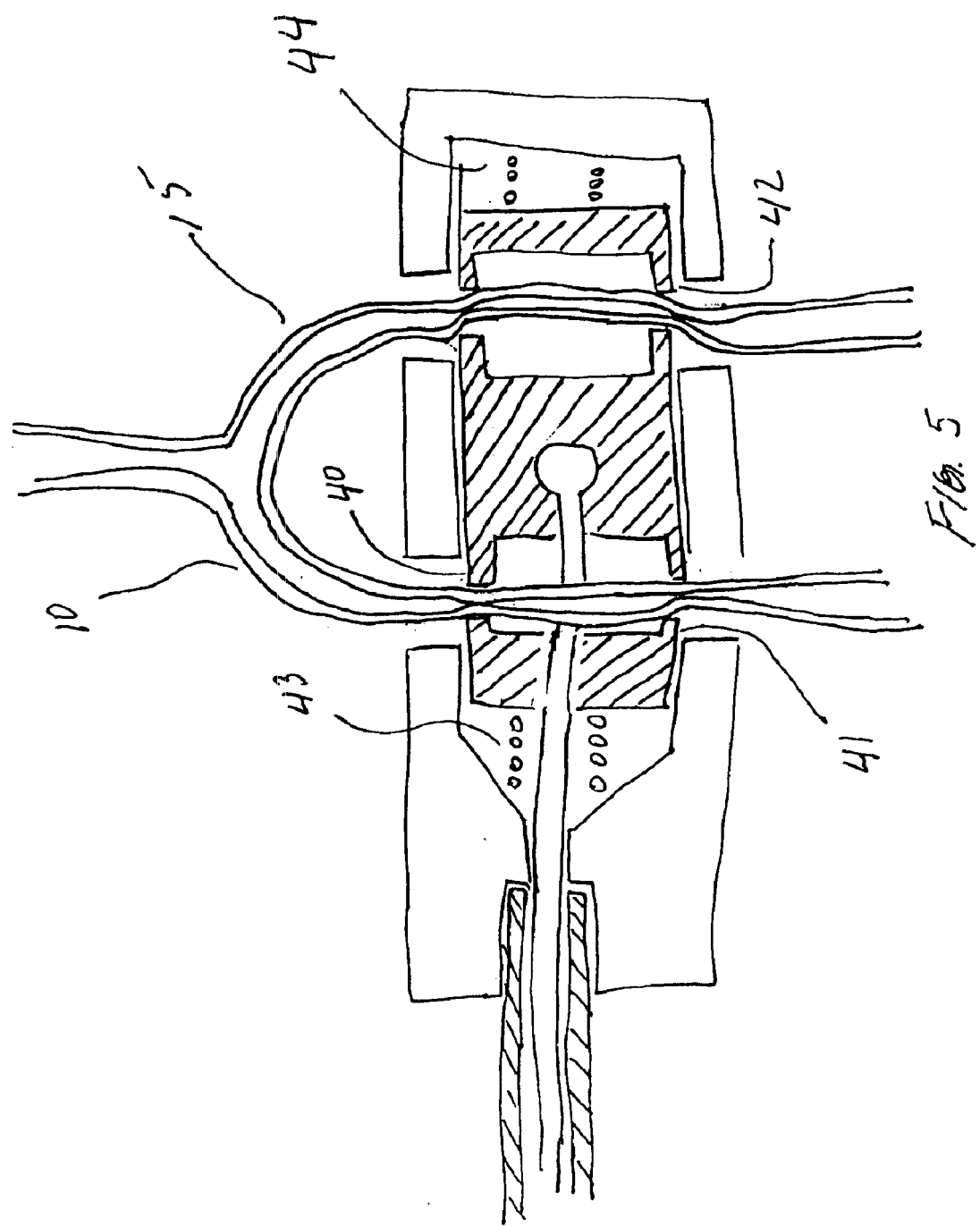
FIG. 5 is a sectional side view of an alternate embodiment of a three-way pinch valve.

Referring to FIG. 5, tubes 10 and 15 are both pinched shut when valve member 40 is in an intermediate position. This is accomplished because valve members 41 and 42 are forced toward valve member 40 by springs 43 and 44 respectively so as to pinch tubes 10 and 15 shut when valve member 40 is in an intermediate position. However, when valve member 40 is positioned so as to fully compress spring 44 thus pinching tube 15 shut, spring 43 is sized such that tube 10 will not be pinched shut. Similarly when valve member 40 is positioned so as to fully compress spring 43 thus pinching tube 10 shut, spring 44 is sized such that tube 15 will not be pinched shut.

Those skilled in the art will further understand that the use of resilient tubing as a fluid carrying vessel assists in allowing fluid flow through the tubes in that the tubing will elastically return to its substantially normal shape upon release of the closing force thereon. However, in some applications tubing which is not resilient may be used as a fluid carrying vessel with the present invention. For example, if the pressure of the fluid being contained by the tube is sufficient to force the tube to an open condition when a given spaced pair of valve members changes from a closed position to an open position, resilient tubing is not required. Of course, it is also possible for a valve itself to serve as a fluid carrying vessel in some applications. These alternatives and others being within the scope of the present invention.

Figure 6:
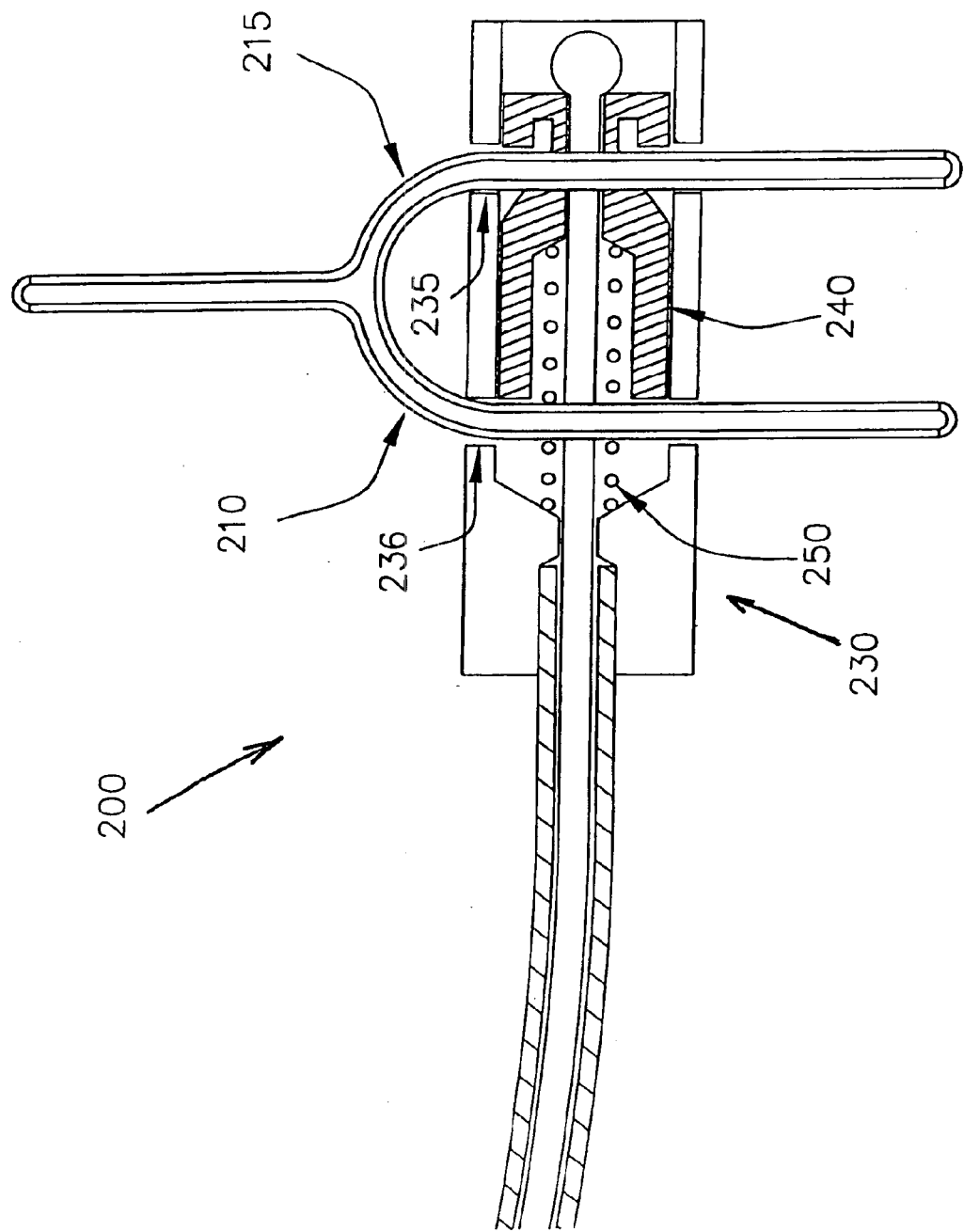
FIG. 6 is a sectional side view of an alternate embodiment of a three-way pinch valve.

FIG. 6 shows a side sectional view of an alternate embodiment of the invention as three-way pinch valve 200. Pinch valve 200 is structurally equivalent to pinch valve 5 of FIG. 1 with the exception of the respective first valve member. Specifically, first valve member 240 of three-way pinch valve 200 is shaped such that when first valve member 240 is in its first position, fluid is permitted to flow through both resilient tube 210 and resilient tube 215. Further, as a result of the changed shape, a different part of the housing serves as the second valve member to operate with first valve member 240 a spaced valve member pair. This is shown by second valve member 235 of housing 230, which is on the opposite side of the passageway with respect to second valve member 35 of housing 30 shown in FIG. 1, and by third valve member 236.

Figure 7:
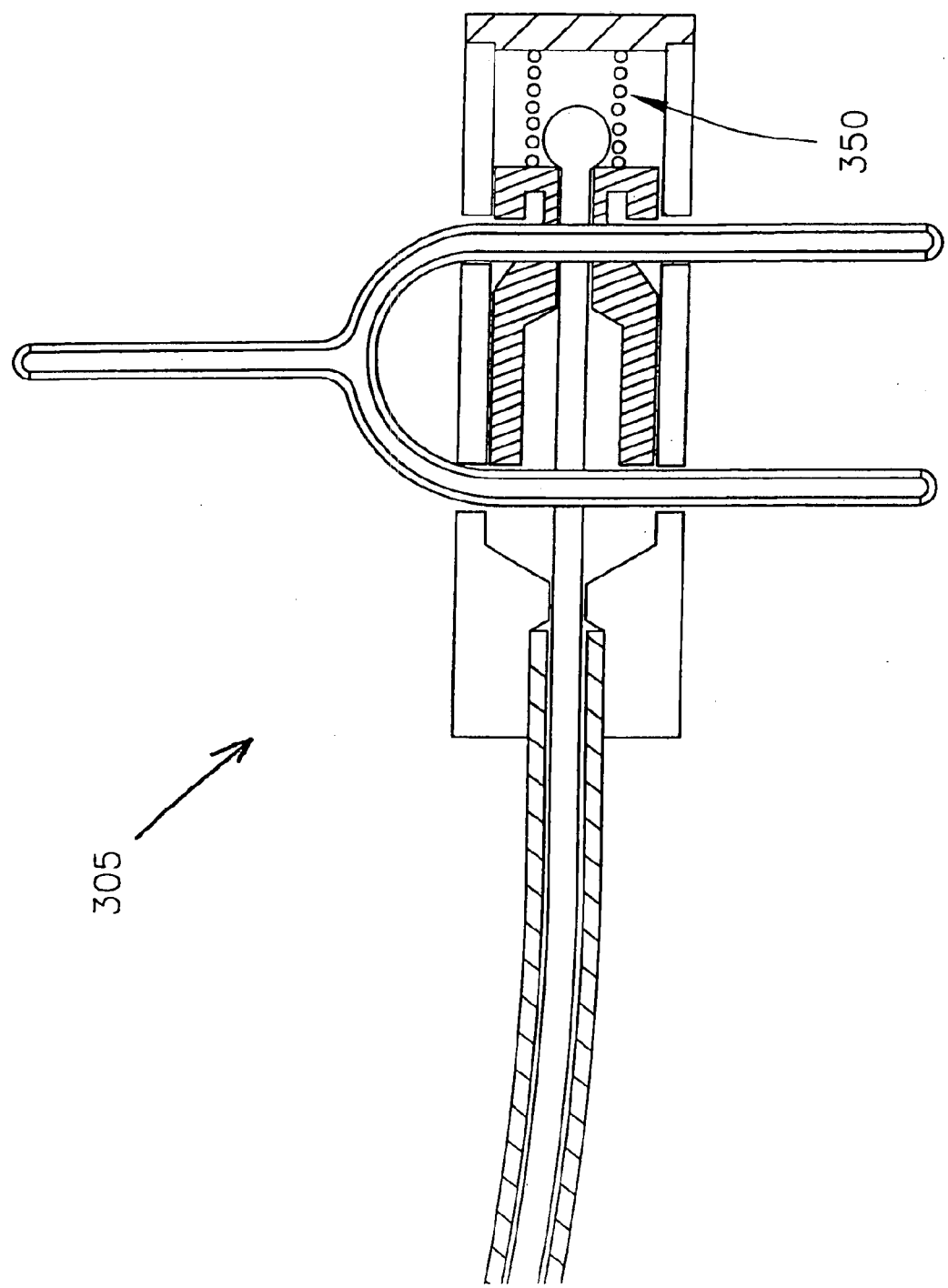
FIG. 7 is a sectional side view of a pinch valve showing an alternate embodiment of the biasing means.

It will be appreciated by those of skill in the art that the first valve member of the present invention may be fashioned which would result in fluid not being allowed to flow through any resilient tubes when the valve is in its first position. Additionally, the invention may be used in conjunction with other embodiments. For example, referring to FIG. 7, alternate embodiment three-way pinch valve 305 is shown. Spring 350 of three-way pinch valve 305 is of the type which resists expansion in contrast to spring 250 of FIG. 6 which is of the type which resists compression. However, spring 350 still serves to bias first valve member 240 with respect to second and third valve members 235 and 236. Several alternate embodiments which are obvious to those skilled are possible with respect to the relationship of the cable, the biasing means, and the spaced valve member pairs. The salient characteristic being the ability to use the cable to overcome the force of the biasing means, thus effecting relative movement between the first valve member (s) and the second valve member(s). All of these variations are within the scope of the present invention.

Figure 8:
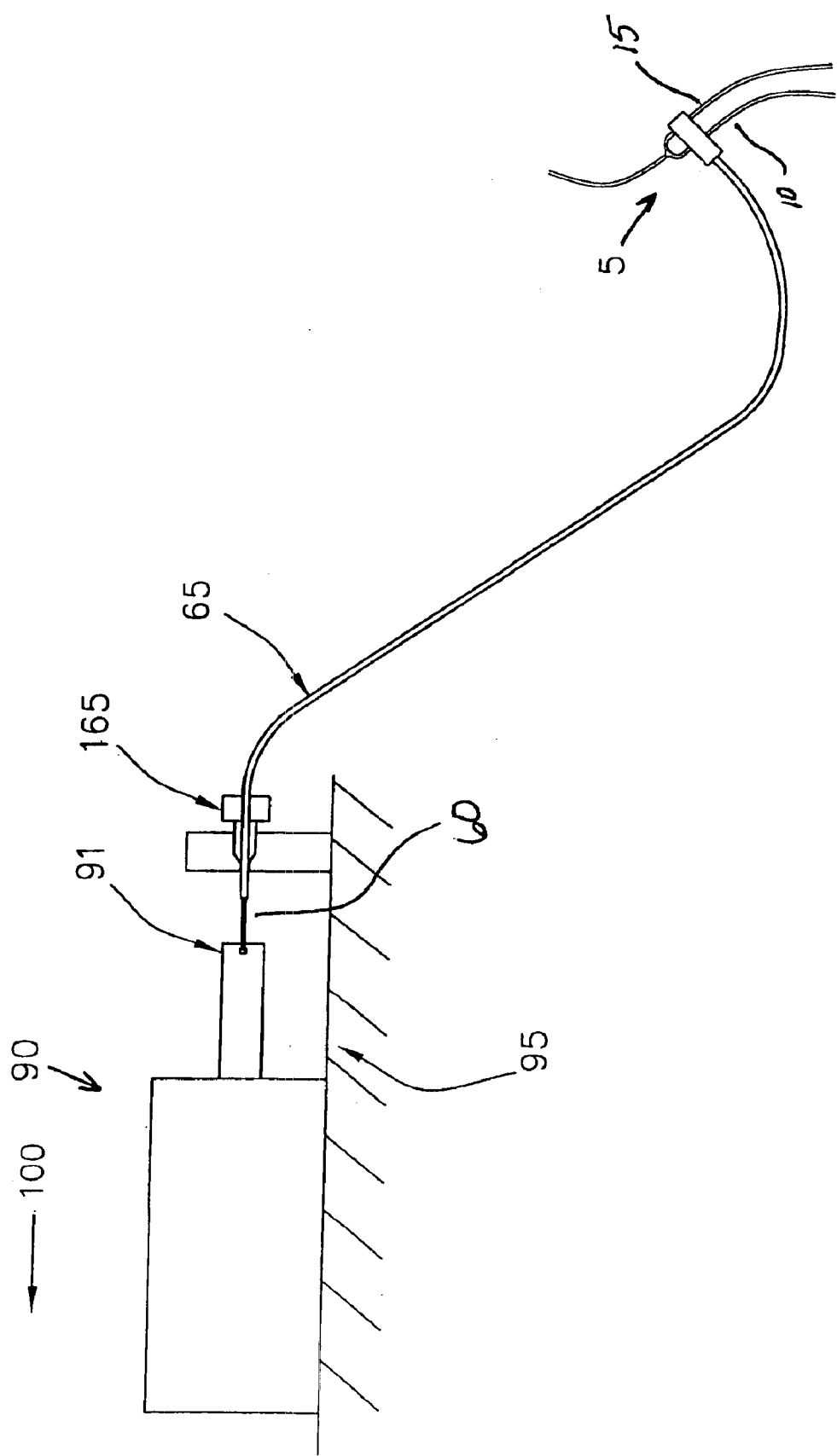
FIG. 8 is a diagrammatic view of one embodiment of a three-way pinch valve connected to a remote motorized actuator wherein the valve's position with respect to the actuator is not fixed.

Referring now to FIG. 8, three-way pinch valve 5 of the embodiment of FIGS. 1 and 2 is shown configured for remote operation. In this embodiment, means for activating 90, which may be an actuating solenoid such as a tubular pull solenoid manufactured by Guardian Electronic of Woodstock, Ill., is fixedly attached to table 95. Activating means 90 serves as means to move cable 60 between its first and second positions to thereby cause the first and second valve member pairs to move between their first and second positions.

It is impractical in certain applications to fix the location of a pinch valve with respect to its remote activating means. For example, the pinch valve may be attached to a moving object or animal as in pharmacokinetics research on a freely moving animal. Referring again to FIG. 1, an embodiment of the present invention is shown which is appropriate for applications where movement between the activator and the pinch valve is allowed or desired. In this embodiment, sleeve 65 comprises a means for slidably constraining cable 60. Sleeve 65 passes through aperture 70 of housing 30, and abuts ledge 67 of housing 30. Sleeve 65 is of the type material which is flexible but not readily compressed such as 0.062 inch OD by 0.030 inch ID PEEK™ tubing manufactured by Upchurch Scientific of Oak Harbor, Wash. Consequently, the length of sleeve 65 remains relatively constant under a range of compressive forces.

Referring now to FIG. 8, sleeve locking device 165 is provided for maintaining sleeve 65 stationary with respect to table 95. However, pinch valve 5 is not fixed in position with respect to activating means 90. Thus, when plunger 91 is moved in the direction of arrow 100, sleeve locking device 165 does not allow sleeve 65 to move with respect to actuating solenoid 90. This results in cable 60 being moved in the direction of arrow 85 as illustrated in FIG. 1. Housing 30 is not allowed to move due to ledge 67 abutting sleeve 65 which is a non-compressible material and which is held immobile with respect to actuating solenoid 90 of FIG. 8 by sleeve locking device 165. Consequently, the linear distance from actuating solenoid 90 to three-way pinch valve 5 along sleeve 65 remains constant throughout the movement of plunger 91. This results in first valve member 40 of three-way pinch valve 5 being forced to its second position by remote operation.

In operation, actuation of actuating solenoid 90 causes plunger 91 to move in the direction of arrow 100, resulting in movement of first valve member 40 of three-way pinch valve from its first position to its second position as described above. Deactivation of actuating solenoid 90 causes plunger 91 to move in the opposite direction of arrow 100, resulting in movement of first valve member 40 from its second to its first position. Thus, fluid flow through resilient tubes 10 and 15 is remotely controlled by use of activating solenoid 90.

It will be appreciated by those of skill in the art that any number of activating mechanisms will work with the present invention, such as, but not limited to, manual manipulation, a worm gear motor, or a motor and cam. The salient characteristic of the activating means being the ability to force cable 60 to move in the direction of arrow 100. Accordingly, those of skill in the relevant art will recognize that the activating means must be sized such that the resilient force of the tube or tubes being acted upon by the pinch valves plus the fluid pressure within the pinch valves can be overcome. Moreover, the friction of the cable within the sleeve must be overcome, the friction increasing as the shape of the sleeve becomes more tortuous.

Although the embodiments of the present invention described herein have exemplified three-way pinch valves, it will be appreciated by those of skill in the art that the present invention may be embodied in other valve types such as, but not limited to, two-way pinch valves. A two-way pinch valve requires only one spaced valve member pair comprising primary and secondary spaced valve members. For example, the embodiment of the invention shown in FIG. 1 operates as a two-way pinch valve by eliminating resilient tube 10. First valve member 40 is the primary spaced valve member and second valve member 35 is the secondary spaced valve member in this embodiment of a two-way pinch valve. Flow of fluid through resilient tube 15 is controlled in the same fashion as three-way pinch valve 5 which is described above. Moreover, although operation of a single valve by a single actuating means has been described, it is possible to control operation of several valves either by a single actuating means or with a plurality of actuating means. These and other variations being within the scope of the present invention.

It will be appreciated by those skilled in the art that the valve of the present invention is lightweight and inexpensive to manufacture and maintain while being extremely reliable. The valve does not require precise alignment or keying in order to ensure correct operation, and can be configured such that it is free to move with respect to its activating mechanism. Finally, the valve is easily adapted for use with many control systems, including applications requiring miniaturization or remote operation, with no loss of the above advantages.

What is claimed is:

1. A valve for controlling fluid flow, comprising:
a first pair of spaced valve members comprising a primary and a secondary spaced valve member, the valve members capable of being relatively positioned in at least an open position and a closed position, such that when the members are in the open position fluid is permitted to flow, and when the members are in the closed position fluid is not permitted to flow;
a first biasing means for biasing the first pair of spaced valve members toward either the open or closed position, the first biasing means operably connected to the primary valve member of the first pair of spaced valve members; and
a first flexible cable operably connected to the primary valve member of the first pair of spaced valve members for movement of the primary valve member with respect to the secondary valve member, the cable movable between a first position and a second position, such that when the cable is in the first position the first pair of spaced valve members are in the open position and when the cable is in the second position the first pair of spaced valve members are in the closed position;
a first activating means, the first activating means operably connected to the first cable, the first activating means having a first and a second position, such that when the first activating means is in the first position, the first cable is in the first position, and when the first activating means is in the second position, the first cable is in the second position;
means for slidably constraining the first cable, the constraining means comprising a first end and a second end, the first end fixedly aligned with the primary valve member of the first pair of spaced valve members, the second end fixedly aligned with the activating means, such that the linear distance from the first activating means to the primary valve member of the first pair of spaced valve members along the constraining means is constant, and when the first cable is moved from the first position to the second position or from the second position to the first position, the first cable slides within the constraining means;
wherein the valve is a pinch valve and the first pair of spaced valve members are spaced such that a fluid carrying vessel may be located within the space between the primary and secondary spaced valve members such that when the members are in the open position and a fluid carrying vessel is located between the primary and the secondary spaced valve members, fluid is free to flow within the fluid carrying vessel and when the members are in the closed position and a fluid carrying vessel is located between the primary and the secondary spaced valve members, fluid is not permitted to flow within the fluid carrying vessel.

2. A valve according to claim 1, wherein:
the first biasing means is fixedly connected to the primary valve member of the first pair of spaced valve members; and
the first cable is fixedly connected to either the primary valve member of the first pair of spaced valve members or the first biasing means.

3. A valve according to claim 1, the secondary valve member of the first pair of spaced valve members comprising:
means for accommodating the primary valve member, the means for accommodating having an-aperture therethrough, such that the first cable may pass through the aperture and such that when the primary valve member of the first pair of spaced valve members is accommodated by the secondary valve member and the first cable is through the aperture and the first cable is moved from the first position to the second position or from the second position to the first position, the first cable moves within the aperture.

4. A valve according to claim 1, wherein the first activating means comprises a solenoid.

5. A valve according to claim 1, wherein the means for slidably constraining the cable comprises a flexible, noncompressible sleeve.

6. A valve according to claim 1, wherein:
the first pair of spaced valve members are capable of being relatively positioned in at least one position intermediate the open position and the closed position, such that when the members are in the intermediate position, fluid is constrainedly permitted to flow;
the first flexible cable is movable to at least one position intermediate the first position and the second position, such that when the first cable is in the at least one intermediate position the first pair of spaced valve members are in the at least one intermediate position; and
the first activating means comprises at least one intermediate position, such that when the first activating means is in the at least one intermediate position, the first cable is in the at least one intermediate position.

7. A valve according to claim 1, wherein the first pair of spaced valve members, while in the closed position, are engaged in a scissor-like manner such that when a fluid carrying vessel is located between the primary and the secondary spaced valve members and the first pair of spaced valve members is in the closed position, the fluid carrying vessel is pinched in a scissor-like manner such that fluid is not allowed to flow as a result of the scissor-like engagement of the primary and secondary spaced valve members.

8. A valve according to claim 1, wherein the first biasing means is a spring.

9. A method of operating at least one valve comprising the steps of:
providing at least one valve capable of controlling fluid flow, the at least one valve comprising
a pinch valve having a first pair of spaced valve members comprising a primary and a secondary spaced valve member, the valve members capable of being relatively positioned in at least an open position and a closed position, such that when the members are in the open position fluid is permitted to flow, and when the members are in the closed position fluid is not permitted to flow, the first pair of spaced valve members spaced such that a fluid carrying vessel may be located within the space between the primary and secondary spaced valve members such that when the members are in the open position and a fluid carrying vessel is located within the space between the primary and secondary spaced valve members, fluid is free to flow within the fluid carrying vessel and when the members are in the closed position and a fluid carrying vessel is located within the space between the primary and secondary spaced valve members, fluid is not permitted to flow within the fluid carrying vessel,
a first biasing means for biasing the first pair of spaced valve members toward either the open or closed position, the first biasing means operably connected to the primary valve member of the first pair of spaced valve members,
a first flexible cable operably connected to the primary valve member of the first pair of spaced valve members for movement of the primary valve member with respect to the secondary valve member, the cable movable between a first position and a second position, such that when the cable is in the first position the first pair of spaced valve members are in the open position and when the cable is in the second position the first pair of spaced valve members are in the closed position;
providing a first activating means, the first activating means operably connected to the first cable, the first activating means movable between a first and a second position, such that when the first activating means is in the first position, the first cable is in the first position, and when the first activating means is in the second position, the first cable is in the second position,
placing the cable via the activating means in either the first or the second position;
moving the cable to a position in which the cable was not placed; and
moving the members from the closed position to the open position, or moving the members from the open position to the closed position.

10. The method of claim 9, the step of providing at least one valve further comprising the step of providing at least one valve wherein:
the first biasing means is fixedly connected to the primary valve member of the first pair of spaced valve members; and
the first cable is fixedly connected to either the primary valve member of the first pair of spaced valve members or the first biasing means; and
wherein the step of moving the cable comprises the step of providing force sufficient to overcome the biasing means and move the primary valve member.

11. The method of claim 10, the step of providing at least one valve further comprising the step of providing at least one valve wherein:
the secondary valve member of the first pair of spaced valve members comprises a means for accommodating the primary valve member, the means for accommodating having an aperture therethrough, such that the first cable may pass through the aperture and such that when the primary valve member of the first pair of spaced valve members is accommodated by the secondary valve member and the first cable is through the aperture and the first cable is moved from the first position to the second position or from the second position to the first position, the first cable moves within the aperture; and
wherein the step of moving the cable comprises the step of moving the cable within the aperture.

12. The method of claim 9, wherein the step of providing an activating means comprises the step of providing a solenoid, and
wherein the step of moving the cable comprises the step of activating or deactivating the solenoid.

13. The method of claim 9, wherein the step of providing at least one valve further comprises the step of providing:
means for slidably constraining the first cable, the constraining means comprising a first end and a second end, the first end fixedly aligned with the primary valve member of the first pair of spaced valve members, the second end fixedly aligned with the activating means, such that the linear distance from the first activating means to the primary valve member of the first pair of spaced valve members along the constraining means is constant, and when the first cable is moved from the first position to the second position or from the second position to the first position, the first cable slides within the constraining means, and
wherein the step of moving the cable comprises the step of sliding the cable within the constraining means.

14. The method of claim 13, wherein the step of providing means for slidably constraining the cable comprises the step of providing a flexible, non-compressible sleeve and
wherein the step of sliding the cable within the constraining means comprises the step of sliding the cable within the flexible, non-compressible sleeve.

15. The method of claim 9, wherein:
the step of providing at least one valve comprises the step of providing a valve wherein:
the first pair of spaced valve members are capable of being relatively positioned in at least one position intermediate the open position and the closed position, such that when the members are in the intermediate position, fluid is constrainedly permitted to flow;
the first flexible cable is movable to at least one position intermediate the first position and the second position, such that when the first cable is in the at least one intermediate position the first pair of spaced valve members are in the at least one intermediate position, and
the step of providing a first activating means farther comprises the step of providing an activating means having at least one intermediate position, such that when the first activating means is in the at least one intermediate position, the first cable is in the at least one intermediate position;

the step of placing the cable comprises the step of placing the activating means in either the first or the second or the at least one intermediate position; and the step of moving the cable to a position in which the cable was not placed comprises the step of moving the activating means to a position in which the activating means was not placed.

16. The method of claim 9, wherein the step of providing a pinch valve comprises the step of providing a pinch valve having a first pair of spaced valve members which, while in the closed position, are engaged in a scissor-like manner such that when a fluid carrying vessel is located between the primary and the secondary spaced valve members and the first pair of spaced valve members is in the closed position, the fluid carrying vessel is pinched in a scissor-like manner such that fluid is not allowed to flow as a result of the scissor-like engagement of the primary and secondary spaced valve members and wherein the step of moving the cable comprises the step of moving the members from a scissor-like engagement of the primary and secondary spaced valve members to the open position, or moving the members from the open position to a scissor-like engagement of the primary and secondary spaced valve members.

17. The method of claim 9, wherein the step of providing at least one valve capable of controlling fluid flow comprises the step of providing at least a first and a second valve capable of controlling fluid flow, each valve comprising a first pair of spaced valve members comprising a primary and a secondary spaced valve member, the valve members capable of being relatively positioned in at least an open position and a closed position, such that when the members are in the open position fluid is permitted to flow, and when the members are in the closed position fluid is not permitted to flow, a first biasing means for biasing the first pair of spaced valve members toward either the open or closed position, the first biasing means operably connected to the primary valve member of the first pair of spaced valve members, and a first flexible cable operably connected to the primary valve member of the first pair of spaced valve members for movement of the primary valve member with respect to the secondary valve member, the cable movable between a first position and a second position, such that when the cable is in the first position the first pair of spaced valve members are in the open position and when the cable is in the second position the first pair of spaced valve members are in the closed position, and wherein the step of providing a first activating means comprises the step of providing an activating means operably connected to the first and the second valve capable of controlling fluid flow, and wherein the step of placing the cable comprises the step of placing the activating means in either the first or the second position; and the step of moving the cable to a position in which the cable was not placed comprises the step of moving the activating means to a position in which the activating means was not placed.

18. The method of claim 17 wherein the step of placing the cable comprises the step of placing the activating means in the first position for the first valve capable of controlling fluid flow and in the second position for the second valve capable of controlling fluid flow.

* * * * *